United States Patent
Fujimori et al.

(10) Patent No.: US 7,675,394 B2
(45) Date of Patent: Mar. 9, 2010

(54) CAPSULE MEDICAL APPARATUS AND CURRENT-CARRYING CONTROL METHOD

(75) Inventors: Noriyuki Fujimori, Nagano (JP); Koichi Shiotani, Nagano (JP)

(73) Assignees: Olympus Medical Systems Corp., Tokyo (JP); Olympus Corporation, Tokyo (JP)

( * ) Notice: Subject to any disclaimer, the term of this patent is extended or adjusted under 35 U.S.C. 154(b) by 127 days.

(21) Appl. No.: 11/639,063

(22) Filed: Dec. 14, 2006

(65) Prior Publication Data

US 2007/0171012 A1 Jul. 26, 2007

(30) Foreign Application Priority Data

Dec. 16, 2005 (JP) ............................. 2005-363919

(51) Int. Cl.
*H01H 1/66* (2006.01)
*H01H 51/00* (2006.01)
*A61B 1/00* (2006.01)
*A61B 1/04* (2006.01)

(52) U.S. Cl. ................... 335/151; 600/101; 600/117

(58) Field of Classification Search ......... 335/151–153; 600/117
See application file for complete search history.

(56) References Cited

U.S. PATENT DOCUMENTS

| | | | | |
|---|---|---|---|---|
| 5,318,557 | A * | 6/1994 | Gross | 604/891.1 |
| 6,918,872 | B2 * | 7/2005 | Yokoi et al. | 600/129 |
| 2001/0007051 | A1 * | 7/2001 | Nakashima | 600/179 |
| 2003/0020810 | A1 * | 1/2003 | Takizawa et al. | 348/68 |
| 2003/0171648 | A1 * | 9/2003 | Yokoi et al. | 600/109 |
| 2003/0171652 | A1 * | 9/2003 | Yokoi et al. | 600/160 |
| 2004/0225190 | A1 * | 11/2004 | Kimoto et al. | 600/177 |
| 2005/0054897 | A1 * | 3/2005 | Hashimoto et al. | 600/118 |
| 2005/0143623 | A1 * | 6/2005 | Kojima | 600/109 |
| 2005/0250991 | A1 * | 11/2005 | Mizuno | 600/160 |
| 2005/0288557 | A1 * | 12/2005 | Yokoi et al. | 600/176 |
| 2006/0167339 | A1 * | 7/2006 | Gilad et al. | 600/101 |
| 2006/0258901 | A1 | 11/2006 | Fujimori et al. | |

FOREIGN PATENT DOCUMENTS

| | | |
|---|---|---|
| JP | 04-008342 | 1/1992 |
| JP | 2003-210395 | 7/2003 |
| WO | WO 2004/086434 A2 | 10/2004 |
| WO | WO 2005/072068 A2 | 8/2005 |

* cited by examiner

*Primary Examiner*—Elvin G Enad
*Assistant Examiner*—Alexander Talpalatskiy
(74) *Attorney, Agent, or Firm*—Scully, Scott, Murphy & Presser, P.C.

(57) ABSTRACT

An object of the present invention is to readily initiate an operation of a capsule medical apparatus which is inserted into a subject and executes a predetermined function. In a capsule endoscope 3 according to the present invention, a reed switch 14 connected to a power supply unit and a function executing unit is arranged parallel to a direction of a longitudinal axis t of a capsule-like casing 16 in the substantially cylindrical capsule-like casing 16 of the capsule endoscope 3. A pair of movable electrodes of the reed switch 14 operates according to magnetic induction of a magnetic field of a magnet 6 applied substantially parallel to the direction t of the longitudinal axis of the capsule-like casing 16, and come into contact with each other. As a result, power supply from the power supply unit to the function executing unit is allowed.

4 Claims, 10 Drawing Sheets

CAPSULE MEDICAL APPARATUS AND CURRENT-CARRYING CONTROL METHOD

CROSS-REFERENCE TO RELATED APPLICATIONS

This application is based upon and claims the benefit of priority from Japanese Patent Application No. 2005-363919, filed Dec. 16, 2005, the entire contents of which are incorporated herein by reference.

BACKGROUND OF THE INVENTION

1. Field of the Invention

The present invention relates to a capsule medical apparatus which is inserted inside a subject and operates on supplied power to execute a predetermined function, and a current-carrying control method thereof.

2. Description of the Related Art

In recent years, a swallowable capsule medical apparatus has been proposed in a field of endoscope. One of the capsule medical apparatuses is a capsule endoscope which has an imaging function and a radio communication function provided inside a capsule-like casing. The capsule endoscope is swallowed by a subject (human body) from the mouth for observation (examination), moves through inside body cavities such as internal organs, e.g., a stomach and a small intestine, following peristaltic movements thereof and sequentially captures images until naturally discharged.

Image data acquired through imaging by the capsule endoscope while the capsule endoscope travels through the body cavities inside the body is sequentially transmitted outside by radio communication, and stored in a memory provided outside. When the subject carries a receiver which is provided with a radio communication function and a memory function, the subject can move freely after swallowing the capsule endoscope until discharging the same. After the capsule endoscope is discharged, a doctor or a nurse can make diagnosis by displaying images of internal organs on a screen based on the image data stored in the memory (see Japanese Patent Application Laid-Open No. 2003-210395).

In the capsule endoscope as described above, a reed switch, which operates according to an external magnetic field, is sometimes employed for supplying power to each function executing unit from a power supply. In general, a longitudinal direction of the conventional reed switch is set vertical to a direction of a longitudinal axis of the capsule endoscope, and a direction of a magnetic field and a lead extending direction of the reed switch are required to coincide with each other.

The capsule endoscope is formed rotationally-symmetrical about the direction of the longitudinal axis, and a position in the rotational direction is not particularly defined. Therefore, it is difficult to make the direction of the magnetic field and the lead extending direction of the reed switch coincide with each other. For example, in order to activate the reed switch, it is necessary to move a magnet which generates the magnetic field around the reed switch to check the orientation of the reed switch. Thus, on/off operations of the reed switch are cumbersome.

SUMMARY OF THE INVENTION

An object of the present invention is at least to solve the above problem.

A capsule medical apparatus according to one aspect of the present invention includes a function executing unit that executes a predetermined function, a power supply unit that supplies power to the function executing unit, a main capsule body that houses the function executing unit and the power supply unit, a switch that is housed in the main capsule body, that has a pair of contacts which come into contact with each other and separate from each other according to a magnetic induction of a magnetic field applied from an outside of the main capsule body, and that connects the function executing unit and the power supply unit via the pair of contacts to allow conduction or to shield conduction, and a direction index that indicates a direction of the magnetic field which cause contact and separation of the pair of contacts in a manner recognizable from an outside.

A capsule medical apparatus according to another aspect of the present invention includes a function executing unit that executes a predetermined function, a power supply unit that supplies power to the function executing unit, a main capsule body that houses the function executing unit and the power supply unit, and a switch that is housed in the main capsule body, that has a pair of contacts which come into contact with each other and separate from each other according to a magnetic induction of a magnetic field applied from an outside of the main capsule body, and that connects the function executing unit and the power supply unit via the pair of contacts to allow conduction or to shield conduction, wherein a lead extending direction of a lead that extends from the pair of contacts is substantially parallel to a direction of a longitudinal axis of the main capsule body.

A capsule medical apparatus according to still another aspect of the present invention includes a function executing unit that executes a predetermined preset function, a power supply unit that supplies power to the function executing unit, a switch that connects the function executing unit and the power supply unit so as to allow for conduction and to shield the conduction, and a main capsule body that is substantially cylindrical in shape, that is formed in a rotationally symmetrical shape about a direction of a longitudinal axis, and houses the function executing unit, the power supply unit, and the switch, wherein the switch switches over a conduction state and a conduction-shielded state of the power supply unit and the function executing unit according to a magnetic induction of a magnetic field applied substantially parallel to the switch from outside the main capsule body in the direction of the longitudinal axis.

A current-carrying control method of a capsule medical apparatus according to still another aspect of the present invention includes, when the capsule medical apparatus is provided with a main capsule body in which a function executing unit that executes a predetermined function, a power supply unit that supplies power to the function executing unit, and a switch that connects the function executing unit and the power supply unit so as to allow for conduction and shield conduction therebetween are provided, recognizing a direction of a magnetic field which works on the switch, controlling the conduction and shielding of the conduction between the power supply unit and the function executing unit by making the magnetic field in a direction based on a result of the recognizing work on the switch from the outside of the main capsule body so as to operate the switch.

A current-carrying control method of the capsule medical apparatus according to still another aspect of the present invention includes arranging a switch which is connected between a function executing unit that executes a predetermined function and a power supply unit that supplies power to the function executing unit, parallel to a direction of a longitudinal axis of a main capsule body, inside the main capsule body which is substantially cylindrical in shape and is formed rotationally symmetrical in shape about the direction of the longitudinal axis, and controlling conduction and shielding of the conduction between the power supply unit and the function executing unit by applying a magnetic field which is substantially parallel to the direction of the longitudinal axis to the switch from an outside of the main capsule body and operating the switch according to an effect of the magnetic field.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of a capsule medical apparatus and a current-carrying control method thereof according to the present invention will be described in detail below with reference to FIGS. 1 to 13. It should be noted that the present invention is not limited to the embodiments below and that various modifications can be made without departing from the scope of the present invention.

First Embodiment

Figure 1:
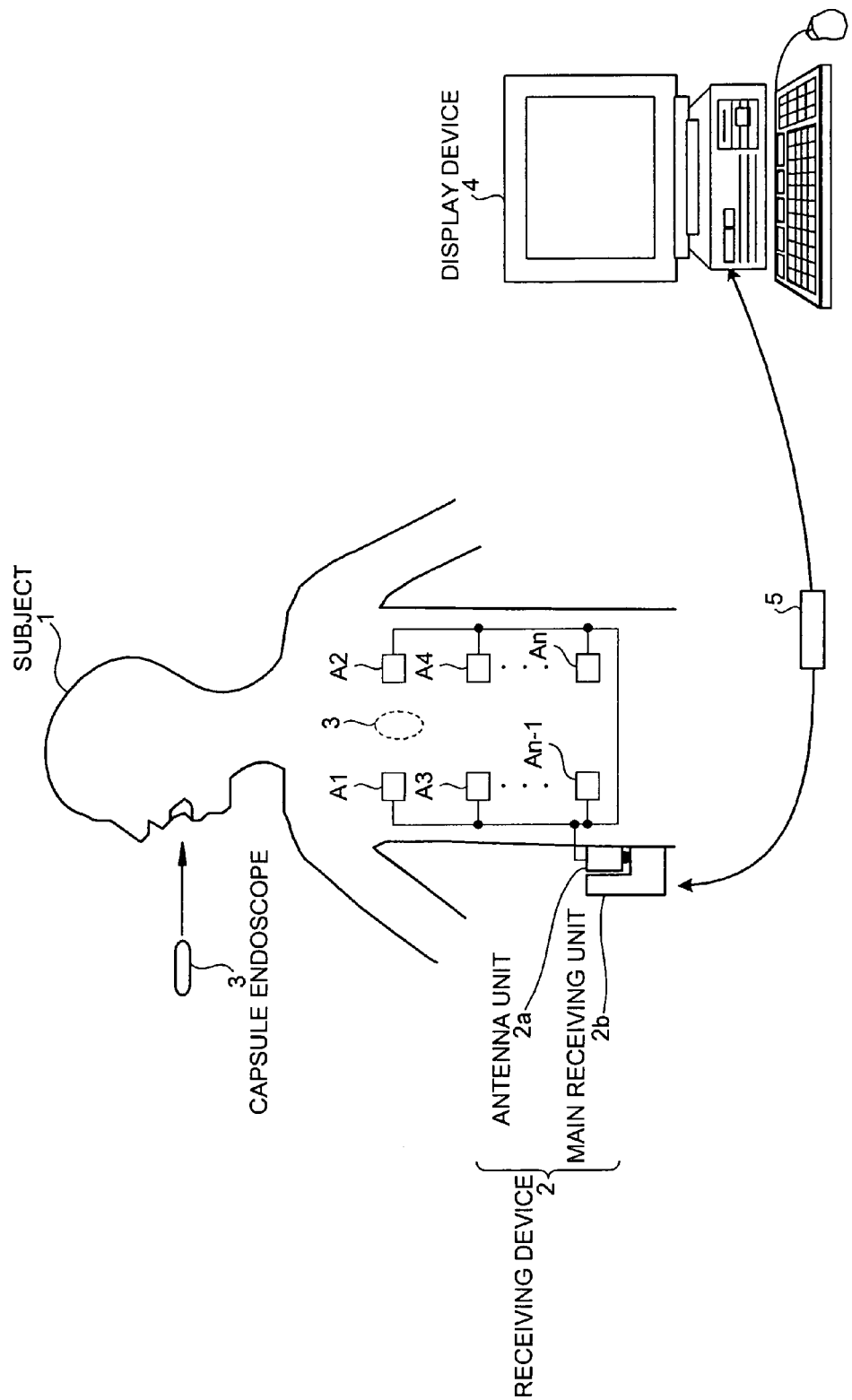
FIG. 1 is a schematic diagram of an overall structure of a radio intra-subject information acquiring system which includes a body-insertable apparatus according to the present invention.

FIG. 1 is a schematic diagram of an overall structure of a radio intra-subject information acquiring system which includes a body-insertable apparatus according to the present invention. In the following, a capsule endoscope, which is inserted into a body cavity from a mouth or the like of a human, i.e., a subject, and captures images of an examined area inside the body cavity, will be described as an example of the body-insertable apparatus of the radio intra-subject information acquiring system. In FIG. 1, the radio intra-subject information acquiring system includes a receiving device 2 which has a radio reception function, and a capsule endoscope 3 which is inserted into a subject 1 to capture images such as body-cavity images and to transmit data such as an image signal to the receiving device 2. Further, the radio intra-subject information acquiring system includes a display device 4 which displays the body-cavity image based on the image signal received by the receiving device 2, and a portable recording medium 5 which serves for data transfer between the receiving device 2 and the display device 4.

The receiving device 2 includes an antenna unit 2a which has plural receiving antennas A1 to An attached onto an external surface of the subject 1 and a main receiving unit 2b which performs, for example, processing of a radio signal received via the plural receiving antennas A1 to An, and the antenna unit 2a and the main receiving unit 2b are connected with each other in a detachable manner via a connector or the like. Each of the receiving antennas A1 to An may be provided, for example, in a jacket the subject 1 can wear, and the subject 1 may put on the receiving antennas A1 to An by wearing the jacket, for example. The receiving antennas A1 to An may be detachable from the jacket. Further, each of the receiving antennas A1 to An may have a main antenna unit at a distal-end portion thereof and the main antenna unit may be housed in an antenna pad which can be pasted onto the body of the subject 1.

The display device 4 serves to display a body-cavity image or the like captured through imaging by the capsule endoscope 3. The display device 4 may have a configuration as a workstation which displays images based on data acquired from the portable recording medium 5. Specifically, the display device 4 may directly display an image on a CRT display, a liquid crystal display, or the like, or alternatively, may be configured to output an image onto other media as in a printer.

The portable recording medium 5 is attachable to and detachable from the main receiving unit 2b and the display device 4, and information can be output from or recorded into the portable recording medium 5 when the portable recording medium 5 is mounted on the main receiving unit 2b or the display device 4. In the first embodiment, the portable recording medium 5 is inserted into the main receiving unit 2b and records data transmitted from the capsule endoscope 3 while the capsule endoscope 3 travels through the body cavities of the subject 1. The portable recording medium 5 is removed from the main receiving unit 2b after the capsule endoscope 3 is discharged from the subject 1, in other words, after the imaging inside the subject 1 is finished, and mounted onto the display device 4. Then, the display device 4 reads out the data recorded in the portable recording medium 5. When the data transfer between the main receiving unit 2b and the display device 4 is performed with the portable recording medium 5 configured with an element such as a Compact Flash® memory, the subject 1 can move more freely during the imaging of the body cavities compared with a case where the main receiving unit 2b and the display device 4 are connected directly by a cable. Though the portable recording medium 5 is employed for the data transfer between the main receiving unit 2b and the display device 4 in the first embodiment, such configuration is not limiting. An embedded storage unit of a different type such as a hard disk can be provided in the main receiving unit 2b, and the main receiving unit 2b and the display device 4 may be connected by a cable or by radio for data transfer.

Figure 2:
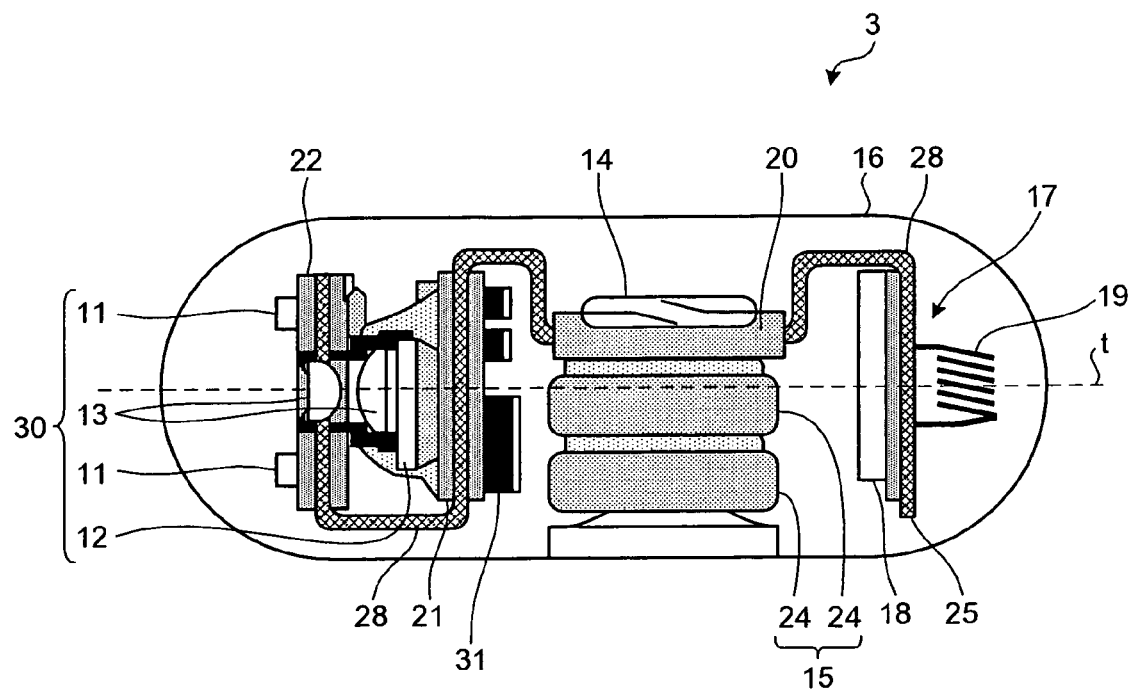
FIG. 2 is a sectional view showing an internal structure of a capsule endoscope according to a first embodiment of the present invention.
Figure 3:
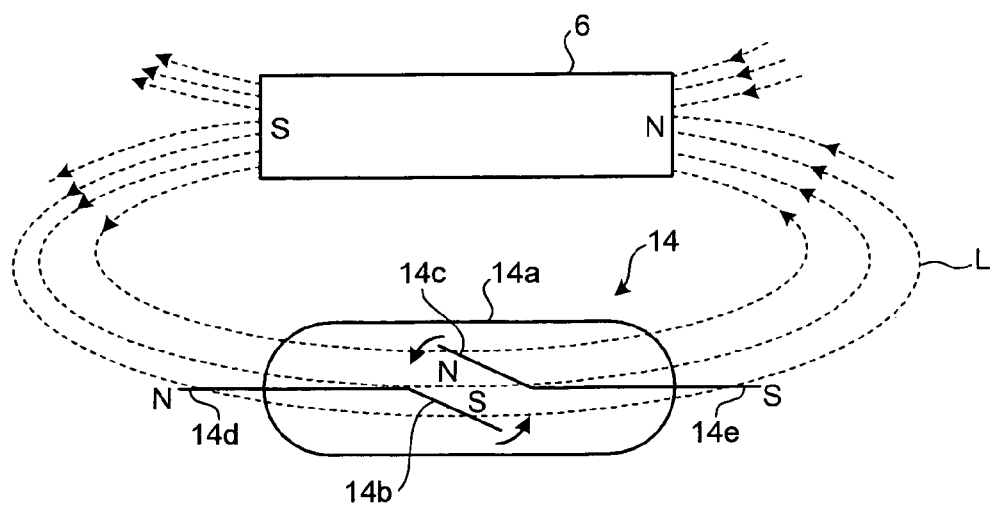
FIG. 3 is an enlarged view of a structure of a reed switch in the vicinity of a magnet.
Figure 4:
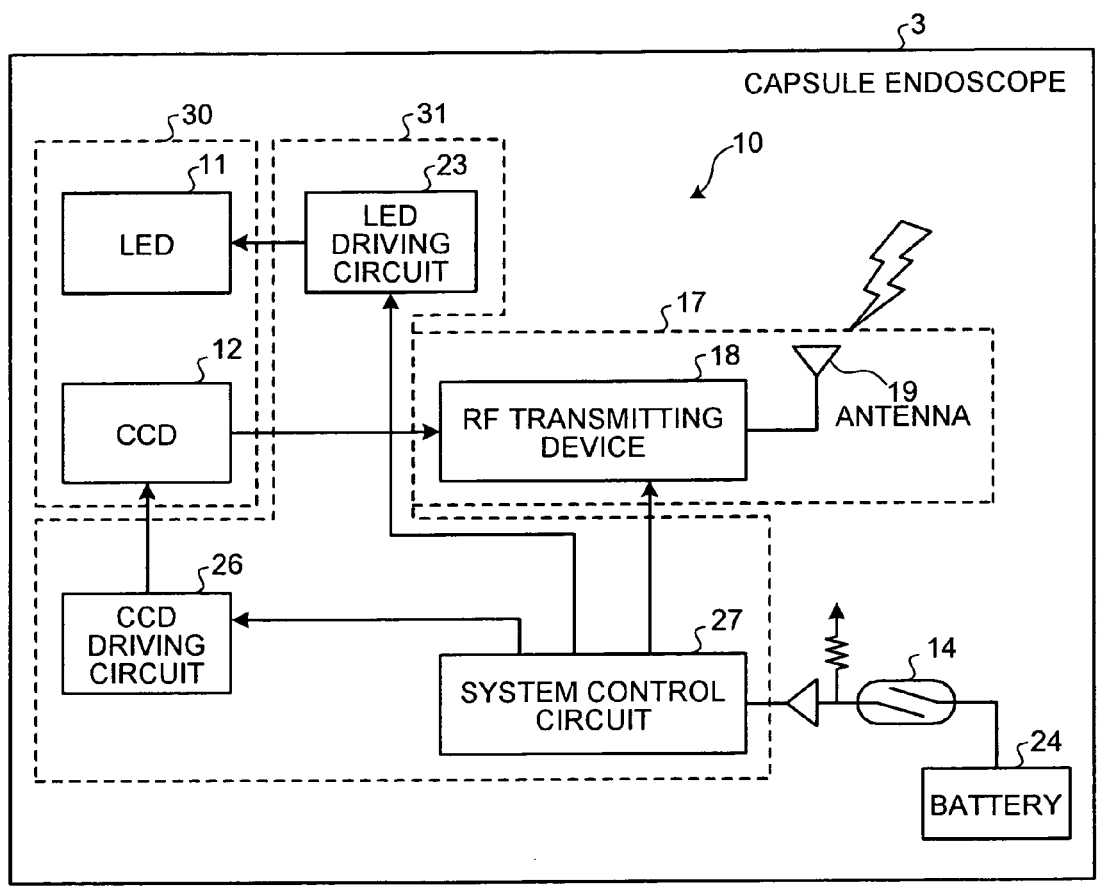
FIG. 4 is a block diagram of an example of a circuit structure of the capsule endoscope shown in FIG. 2.

FIG. 2 is a sectional view of an internal structure of the capsule endoscope 3 according to the first embodiment; FIG. 3 is an enlarged view of a structure of a reed switch 14 in the vicinity of a magnet which is a magnetic body; and FIG. 4 is a block diagram of an example of a circuit structure of the capsule endoscope 3 shown in FIG. 2. The capsule endoscope 3 includes an image sensor 30 as an information acquiring unit provided with an illuminating unit such as an LED 11 to illuminate an interior of the body cavity of the subject 1, an imaging unit such as a CCD 12 to capture an image inside the body cavity, and an optical system device 13 as an optical unit to focus a body-cavity image at an imaging position of the CCD 12, and the capsule endoscope 3 further includes a radio unit 17 which is provided with an RF transmitting device 18 as a transmitter that transmits image data acquired through imaging by the CCD 12 and an antenna 19. The image sensor 30 and the radio unit 17 are connected via the reed switch 14 to a power supply unit 15 which serves as a power supply in such a manner as to allow conduction or shielding of the conduction. The power supply unit 15 supplies power to the image sensor 30, the radio unit 17, and the like. The capsule endoscope 3 is configured so that the above elements are arranged inside a capsule-like casing 16, which is a main capsule body. The image sensor 30, the radio unit 17, and a signal processing/control unit 31 described later are respective portions of a function executing unit 10 according to the present invention.

The reed switch 14 includes, as shown in FIG. 3, an external casing 14a formed of a substantially cylindrical glass tube, for example, leads 14d and 14e that serve as lead-out portions that project from the external casing 14a, and movable electrodes 14b and 14c provided at respective ends of the leads 14d and 14e inside the external casing 14a as a pair of contacts that are movable so as to contact with each other in response to a magnetic field generated in a direction substantially parallel to the direction of the longitudinal axis of the capsule endoscope 3 (capsule-like casing 16). Each of the leads 14d and 14e and the movable electrodes 14b and 14c is formed with an electrically conductive, magnetic member, and the movable electrodes 14b and 14c are inserted into the external casing 14a from outside so as to be arranged along a central axis of the external casing 14a. The leads 14d and 14e and the movable electrodes 14b and 14c are magnetized to be opposite poles according to the magnetic induction of a magnetic field L generated by an approaching magnet 6. For example, when the magnet 6 is brought close as shown in FIG. 3, the lead 14d is magnetized to be an N-pole and the movable electrode 14b is magnetized to be an S-pole, while the lead 14e is magnetized to be an S-pole and the movable electrode 14c is magnetized to be an N-pole. As a result of the magnetization, an end of the movable electrode 14b and an end of the movable electrode 14c move so as to contact with each other.

The reed switch 14 according to the first embodiment is arranged on a surface of a switching board 20 placed substantially at a center of the capsule-like casing 16, with the longitudinal direction thereof being parallel to a direction of a longitudinal axis t of the capsule-like casing 16. The leads 14d and 14e (opposite ends of the movable electrodes 14b and 14c) projecting from the external casing 14a are soldered to wires (not shown), for example, on the switching board 20. Thus, the reed switch 14 is electrically connected to the function executing unit 10 and the power supply unit 15 via the wires. In other words, the reed switch 14 is arranged inside the capsule-like casing 16 so that the lead extending direction of each of the leads 14d and 14e extending from the movable electrodes 14b and 14c is substantially parallel to the direction of the longitudinal axis t of the capsule-like casing 16. Therefore, when the movable electrodes 14b and 14c are brought into contact with each other, power is supplied from the power supply unit 15 to the function executing unit 10 to enable an operation of each element for function execution. The reed switch 14 may be alternatively arranged on a surface of a flexible board 28 described later, for example, and not on the surface of the switching board 20, so that the longitudinal direction thereof is parallel to the direction of the longitudinal axis t of the capsule-like casing 16.

The capsule-like casing 16 includes a transparent semi-spherical dome-like distal-end-cover casing that covers the image sensor 30, for example, and a cylindrical body casing that is engaged with the distal-end-cover casing such that the image sensor 30 and the radio unit 17 are arranged therein with the power supply unit 5 arranged therebetween while the inside of the capsule-like casing 16 maintained in a watertight state. The capsule-like casing 16 is formed in a size swallowable from the mouth of the subject 1. The body casing has a semi-spherical dome-like distal-end portion formed of a colored material which does not allow visible light to pass through, at an end opposite to an opening engaged with the distal-end-cover casing.

The CCD 12 is arranged on an imaging board 21 to capture an image within a range illuminated by the illuminating light emitted from the LED 11. The optical system device 13 consists of imaging lenses that focus an image of the subject on the CCD 12. The LEDs 11 are mounted on an illuminating board 22 at six positions near and around an optical axis of the imaging lens to the right of, the left of, above, and below the optical axis. Further, the image sensor 30 includes the signal processing/control unit 31 on a back side of the imaging board 21 for processing and/or controlling each element, as an internal control unit that controls the image sensor 30 and the RF transmitting unit 18. Further, the switching board 20, the imaging board 21, and the illuminating board 22 are electrically connected with each other as appropriate via the flexible board 28.

The power supply unit 15 consists of two button-type batteries 24 that have a diameter substantially equal to an inner diameter of the body casing, for example. As the battery 24, a silver oxide battery, a rechargeable battery, a power-generating battery, or the like can be employed. The RF transmitting device 18 is arranged on a back side of a radio board 25, for example. The antenna 19 is mounted on the radio board 25, for example.

A circuit structure of the capsule endoscope 3 will be described with reference to FIG. 4. The capsule endoscope 3 includes: the LED 11 and the CCD 12 as the image sensor 30; an LED driving circuit 23 that controls a driven state of the LED 11, a CCD driving circuit 26 that controls a driven state of the CCD 12, and a system control circuit 27 that controls the operations of the LED driving circuit 23, the CCD driving circuit 26, and the RF transmitting device 18 as the signal processing/control unit 31; and the RF transmitting device 18 and the antenna 19 as the radio unit 17.

The system control circuit 27 allows the capsule endoscope 3 to work so that the CCD 12 acquires image data of an examined area illuminated by the LED 11 while the capsule endoscope 3 is inside the subject 1. The image data acquired is converted into an RF signal by the RF transmitting device 18, and the RF signal is transmitted via the antenna 19 to the outside of the subject 1. Further, the capsule endoscope 3 includes the battery 24 which supplies power to the system control circuit 27 via the reed switch 14, and the system control circuit 27 has a function of distributing the driving power supplied from the battery 24 to other elements (LED driving circuit 23, CCD driving circuit 26, and RF transmitting device 18).

Further, the capsule endoscope 3 may include a latch circuit (not shown) arranged between the power supply unit 15 and the function executing unit 10 and having the reed switch 14 as a part thereof, such that the latch circuit is turned on in response to an input of a signal, which serves as a control signal, generated as a result of a contact between the movable electrodes 14b and 14c of the reed switch 14 when the magnet 6 is brought close to the reed switch 14, and that the latch circuit is retained in an on-state thereafter to continuously supply the power from the power supply unit 15 to the function executing unit 10. Such configuration allows for an efficient power supply without being negatively affected by a contact resistance between the movable electrodes 14b and 14c.

Figure 5:
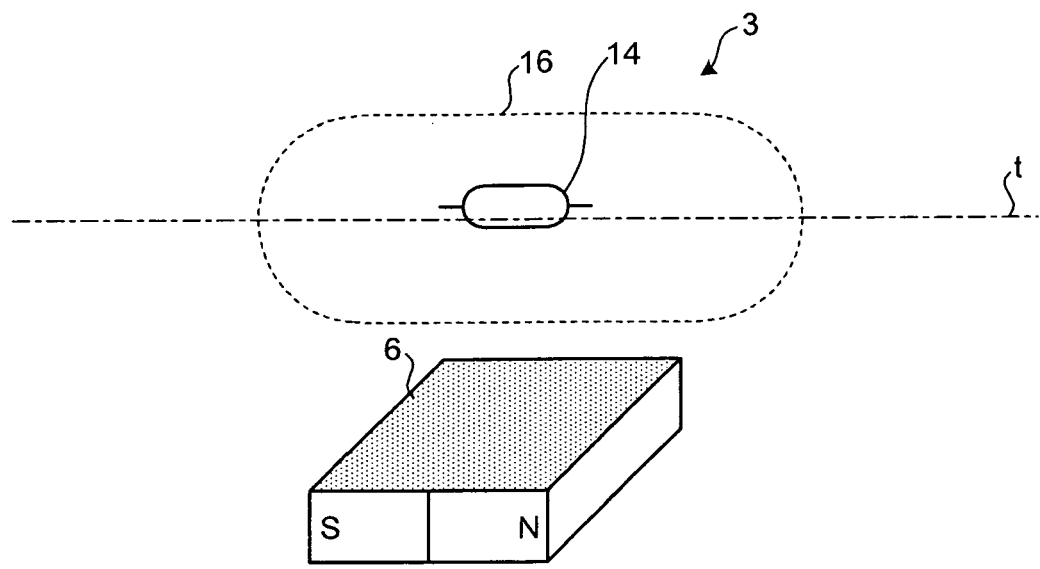
FIG. 5 is a schematic diagram illustrating a power-supply operation of a reed switch according to the first embodiment.

When the external magnet 6 is brought close to the reed switch 14 of the capsule endoscope 3 with the above structure, as shown in FIG. 5, while the external magnet 6 kept parallel to the direction of the longitudinal axis t of the capsule-like casing 16 of the capsule endoscope 3, and the magnet 6 enters an operable range of the reed switch 14, the leads 14d and 14e and the movable electrodes 14b and 14c are magnetized to be different poles (N-pole and S-pole), respectively, according to the magnetic induction of the magnetic field of the magnet 6 applied in a substantially parallel direction to the direction of the longitudinal axis t. The magnetization makes the movable electrodes 14b and 14c pulled to each other (in directions shown by solid arrows of FIG. 3) and the movable electrodes 14b and 14c are brought into contact with each other. As a result, the power supply unit 15 and the function executing unit 10 are electrically connected via the reed switch 14, to allow for the power supply from the power supply unit 15 to the function executing unit 10.

A current-carrying control method of the capsule endoscope according to the first embodiment will be described. First, the capsule endoscope 3 is configured so that the function executing unit 10 (image sensor 30, radio unit 17, signal processing/control unit 31, and the like) and the reed switch 14 are arranged inside the capsule-like casing 16, as shown in FIG. 2 mentioned above. The reed switch 14 has the movable electrodes 14b and 14c that are movable in response to an application of a magnetic field parallel to the extending direction of the leads. The reed switch 14 is arranged within the capsule-like casing 16 of the substantially cylindrical capsule endoscope 3 which is formed in a rotationally symmetrical shape about the direction of the longitudinal axis t, so that the extending direction of the leads is substantially parallel to the direction of the longitudinal axis t (switch unit arranging step). The reed switch 14 is, as described earlier, electrically connected to the function executing unit 10 and the power supply unit 15.

Then, the magnet 6 arranged outside the capsule endoscope 3 is brought closer to or away from the reed switch 14 in order to magnetically operate the reed switch 14, whereby a conduction state or a conduction-shielded state of the function executing unit 10 and the power supply unit 15 via the reed switch 14 is controlled (current-carrying control step). In the current-carrying control step, the magnet 6 arranged outside the capsule endoscope 3 is brought closer to the reed switch 14 while the direction of magnetic field of the magnet 6 is kept substantially parallel to the direction of the longitudinal axis t of the capsule-like casing 16, as shown in FIGS. 3 and 5. When the magnet 6 enters the operable range of the reed switch 14, the movable electrodes 14b and 14c of the reed switch 14 are magnetized to be different poles (N-pole and S-pole) according to the magnetic induction of the magnet 6 which generates a magnetic field applied substantially parallel to the direction of the longitudinal axis t. The magnetization causes the movable electrodes 14b and 14c to be pulled towards each other and to contact, and as a result, the power supply unit 15 and the function executing unit 10 that have been in the conduction-shielded state are brought into an electrically connected state (conduction state) via the reed switch 14. While in the conduction state, the power can be supplied from the power supply unit 15 to the function executing unit 10.

As can be seen from the foregoing, in the first embodiment, the magnet 6 outside the capsule endoscope 3 is brought close to the reed switch 14 while the magnetic field and the direction of the longitudinal axis t of the capsule-like casing 16 are maintained substantially parallel to each other; the movable electrodes 14b and 14c are brought into operation and made to contact with each other according to the magnetic induction of the magnetic field of the magnet 6 applied substantially parallel to the extending direction of the leads of the reed switch 14; whereby the power supply from the power supply unit 15 to the function executing unit 10 is allowed. Therefore, the on/off operations of the reed switch can be realized without the need of confirmation of the orientation of the reed switch, and the operation of the capsule endoscope (more specifically, the operation of the function executing unit 10) can be initiated securely and easily.

Modification of First Embodiment

Figure 6:
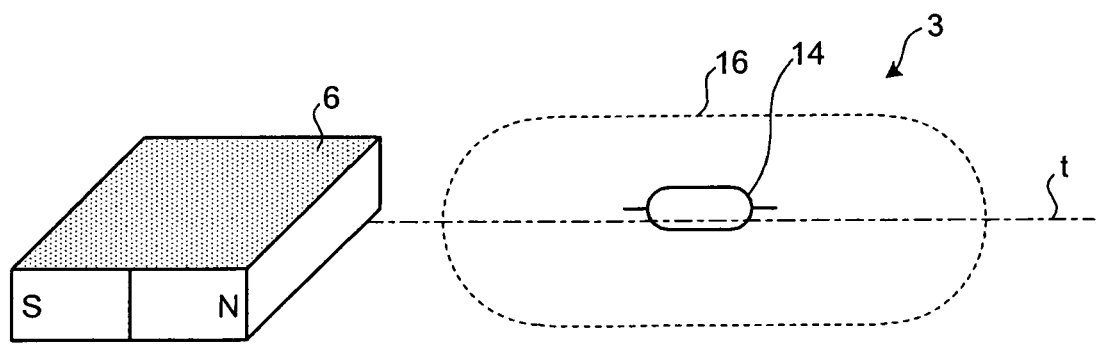
FIG. 6 is a schematic diagram illustrating a power-supply operation of a reed switch according to a modification of the first embodiment.

FIG. 6 is a schematic diagram of a modification of the first embodiment and given for a description of the power supply operation of the reed switch 14. In the modification of the first embodiment as shown in FIG. 6, the magnet 6 is brought closer to the capsule endoscope 3 from the distal-end side where the image sensor 30 is provided, so that the magnetic field of the magnet 6 works on the reed switch 14 arranged in the capsule-like casing 16 in the direction substantially parallel to the direction of the longitudinal axis t of the capsule-like casing 16 of the capsule endoscope 3.

In the modification of the first embodiment, as described above, the magnet 6 outside the capsule endoscope 3 is brought closer to the capsule endoscope 3 from the distal-end side; the movable electrodes 14b and 14c are brought into operation and made to contact with each other according to the magnetic induction of the magnetic field of the magnet 6 applied substantially parallel to the reed switch 14; whereby the power supply from the power supply unit 15 to the function executing unit 10 is allowed. Therefore, similarly to the first embodiment, the on/off operations of the reed switch can be realized without the need of confirmation of the orientation of the reed switch, and the operation of the capsule endoscope (more specifically the operation of the function executing unit 10) can be initiated securely and easily. Depending on the strength of the magnetic field, the magnet 6 may be brought close to the capsule endoscope 3 from a back-end side where the radio unit 17 is provided, for example. The current-carrying control method of the capsule endoscope according to the modification of the first embodiment is the same as that of the first embodiment.

Second Embodiment

Figure 7:
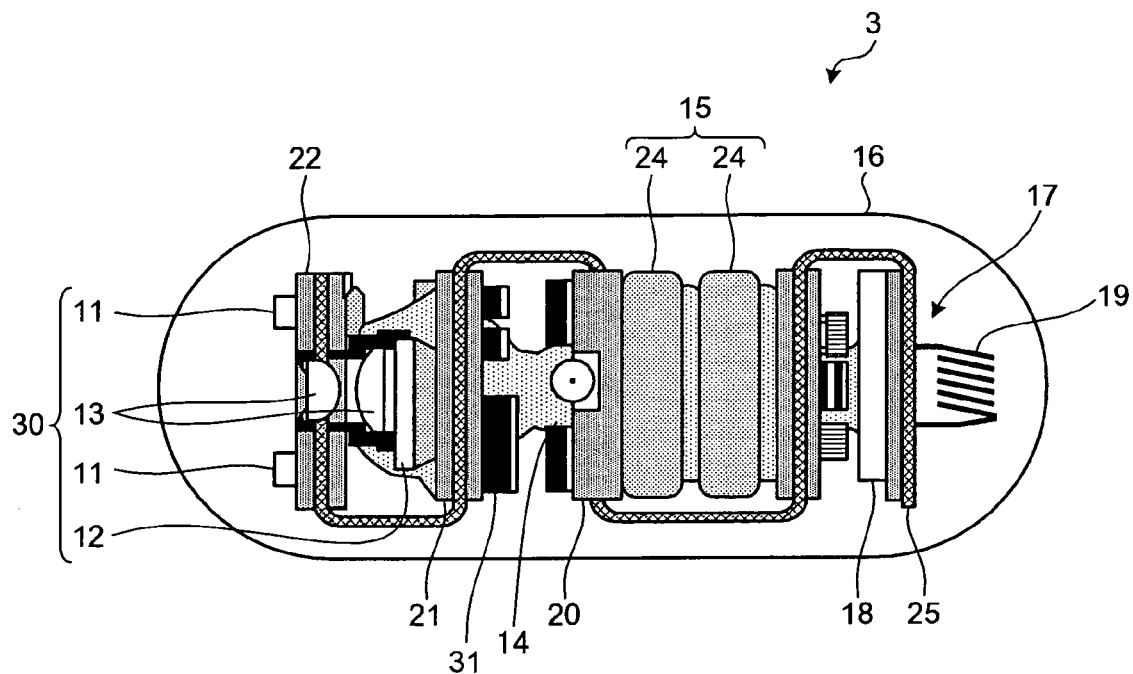
FIG. 7 is a sectional view showing an internal structure of a capsule endoscope according to a second embodiment of the present invention.
Figure 8:
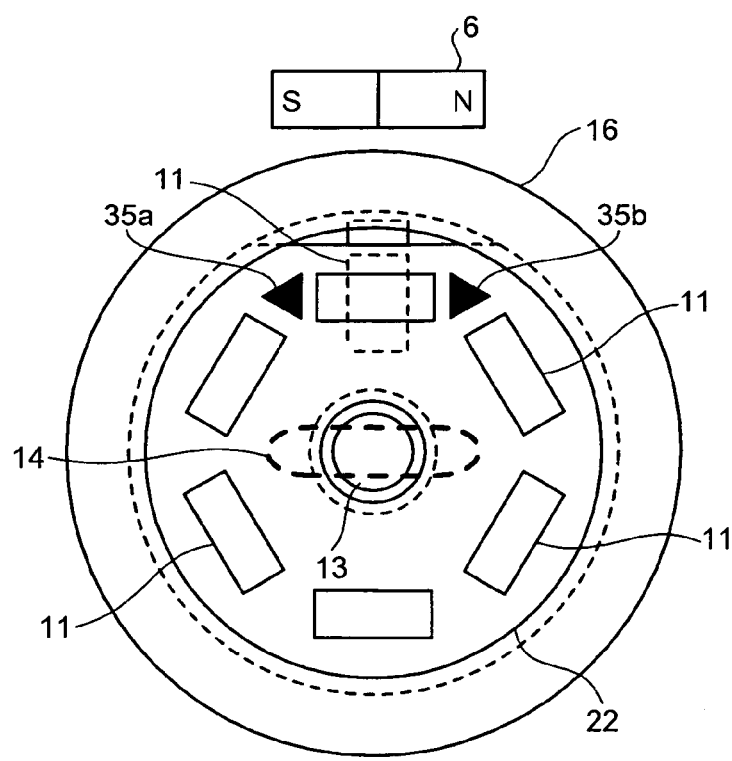
FIG. 8 shows the capsule endoscope of FIG. 7 viewed from a distal-end side where an image sensor is provided.

FIG. 7 is a sectional view of an internal structure of the capsule endoscope 103 according to a second embodiment of the present invention; and FIG. 8 is a sectional view of the capsule endoscope 103 shown in FIG. 7 viewed from the distal-end side where the image sensor 30 is provided. In the second embodiment, as shown in FIGS. 7 and 8, the reed switch 14 is arranged on the switching board 20 provided substantially at the center of the capsule endoscope 103 as in the conventional apparatus, so that the longitudinal direction of the reed switch 14 (i.e., the extending direction of the leads) is vertical to the direction of the longitudinal axis of the capsule-like casing 16 of the capsule endoscope 103. In other respects, the structure of the second embodiment is the same as the structure of the first embodiment, and the same element will be denoted by the same reference character.

As shown in FIG. 8, on a front face of the disk-like illuminating board 22, two triangular indexes 35a and 35b are arranged within an externally recognizable range along with six LEDs 11. The indexes 35a and 35b indicate in a manner recognizable from the outside the direction of the magnetic field of the magnet 6 necessary to make the movable electrodes 14b and 14c, i.e., a pair of contacts of the reed switch 14, move (i.e., move towards each other or away from each other). Specifically, the indexes 35a and 35b show, in a recognizable manner, the orientation (direction of N-pole and S-pole) of the magnet 6 at the time the magnet 6 is brought close to the capsule-like casing 16 to make the movable electrodes 14b and 14c of the reed switch 14 move towards each other or away from each other to switch over the on/off states of the power supply from the power supply unit 15 to the function executing unit 16. Further, the indexes 35a and 35b show the extending direction of leads of the reed switch 14 arranged inside the capsule-like casing 16 at the same time. An operator can easily recognize the direction of the magnet 6 (i.e., direction of a magnetic field applied to the reed switch 14) approaching the capsule-like casing 16 and the extending direction of the leads of the reed switch 14 (angle formed by a central axis of the reed switch 14 and the direction of the longitudinal axis t), by visually checking the indexes 35a and 35b. The indexes 35a and 35b may be formed on the surface of the illuminating board 22 at the time of manufacture of the illuminating board 22, or may formed as a printed pattern through printing on the board surface.

The magnet 6 is brought close to a predetermined position which is substantially at the center of the capsule endoscope 103 based on the indexes 35a and 35b (for example, the magnet 6 is brought close substantially to the center of the capsule endoscope 103 while the S-pole end and the N-pole end of the magnet 6 are kept aligned with the indexes 35a and 35b, respectively, as shown in FIG. 8). Then, the leads 14d and 14e and the movable electrodes 14b and 14c of the reed switch 14 are magnetized to be different poles according to the magnetic induction of the magnetic field of the magnet 6, and the magnetization causes one end of the movable electrode 14b and one end of the movable electrode 14c to move and contact with each other.

A current-carrying control method of the capsule endoscope according to the second embodiment will be described. As shown in FIG. 7 mentioned above, the capsule endoscope 103 is formed so that the function executing unit 10 (image sensor 30, radio unit 17, signal processing/control unit 31, and the like) and the reed switch 14 are arranged inside the capsule-like casing 16. The reed switch 14 has the movable electrodes 14b and 14c that are movable in response to an application of a magnetic field parallel to the extending direction of the leads. The reed switch 14 is arranged within the capsule-like casing 16 of the substantially cylindrical capsule endoscope 103 which is formed in a rotationally symmetrical shape about the direction of the longitudinal axis t, so that the extending direction of the leads is substantially vertical to the direction of the longitudinal axis t (switch unit arranging step). Then, the direction of the magnetic field (i.e., the direction of the magnetic field of the magnet 6 which approaches the reed switch 14 from outside the capsule endoscope 103) which works on the reed switch 14 is vertical to the direction of the longitudinal axis t of the capsule-like casing 16. The reed switch 14 is electrically connected to the function executing unit 10 and the power supply unit 15, as described above.

Then, the operator recognizes the direction of the magnetic field of the magnet 6 that works on the reed switch 14 by visually checking the indexes 35a and 35b formed on the capsule endoscope 103 (more specifically on the illuminating board 22) (direction recognizing step). As shown in FIG. 8, the indexes 35a and 35b are formed on the illuminating board 22 inside the capsule endoscope 103 to indicate in a visually recognizable manner the direction of the magnetic field of the magnet 6 (direction of the N-pole and the S-pole of the magnet 6) that works on the reed switch 14 to move the movable electrodes 14b and 14c of the reed switch 14 towards each other or away from each other, to control the conduction state or the conduction-shielded state of the function executing unit 10 and the power supply unit 15.

Thereafter, the magnet 6 is brought close to or taken away from the reed switch 14 at the outside of the capsule endoscope 103 so as to magnetically operate the reed switch 14, whereby the conduction state or the conduction-shielded state of the function executing unit 10 and the power supply unit 15 is controlled via the reed switch 14 (current-carrying control step). In the current-carrying control step, as shown in FIG. 8, the magnet 6 is brought close to the predetermined position substantially at the center of the capsule endoscope 103 while the S-pole and the N-pole of the magnet 6 is kept aligned with the indexes 35a and 35b as described above. When the magnet 6 enters the operable range of the reed switch 14, the magnetic field, which is substantially parallel to the extending direction of the leads of the reed switch 14 (i.e., a direction substantially vertical to the direction of the longitudinal axis t), is applied to the reed switch 14 from the magnet 6, and the movable electrodes 14b and 14c of the reed switch 14 are magnetized to be different poles (N-pole, S-pole) according to the magnetic induction of the magnetic field of the magnet 6. The magnetization causes the movable electrodes 14b and 14c to be pulled towards each other to contact, and as a result, the power supply unit and the function executing unit 10 that have been in the conduction-shielded state are brought into an electrically connected state (conduction state) via the reed switch 14. While in the conduction state, the power supply from the power supply unit 15 to the function executing unit 10 is allowed.

As can be seen from the foregoing, in the second embodiment, the indexes 35a and 35b are arranged within the range recognizable from outside the capsule endoscope 103 so as to indicate the direction of the magnetic field of the magnet 6 necessary for moving (bringing in contact with each other or separating from each other) the movable electrodes 14b and 14c, i.e., a pair of contacts of the reed switch 14. When the magnet 6 is brought close to the reed switch 14 in such a manner that the direction indicated by the indexes 35a and 35b is kept substantially equal to the direction of the magnetic field, then, the magnetic field of the external magnet 6 is applied to the reed switch 14 in a direction parallel to the extending direction of the leads, whereby the movable electrodes 14b and 14c can be moved and brought into contact with each other according to the magnetic induction of the magnetic field. As a result, the power supply from the power supply unit 15 to the function executing unit 10 is allowed.

Therefore, the operator can easily check the orientation of the reed switch from the outside to realize the on/off operations of the reed switch, whereby the operation of the capsule endoscope (more specifically, the operation of the function executing unit 10) can be initiated securely and easily.

In the second embodiment, the direction of the magnetic field of the magnet 6 (i.e., orientation of the reed switch 14) is indicated by the indexes 35*a* and 35*b*. The present invention, however, is not limited thereto, and the direction of the magnetic field of the magnet 6 can be indicated by a change in position or direction of other elements. As an example of such modification according to the present invention, a specific LED 11 among the LEDs 11 may be arranged such that the longitudinal direction thereof is aligned with a predetermined radial direction of the disk-like illuminating board 22 as shown by a dotted line in FIG. 8, so that the specific LED 11 indicates the direction of the magnetic field of the magnet 6 (orientation of the reed switch 14). When such modification is adopted, the LED 11 is preferably arranged outside a range of visual field which is determined depending on optical characteristics of the imaging lens focusing the subject image on the CCD 12.

In the above, the description of the second embodiment is provided based on the reed switch which operates according to the magnetic field. Other types of switches are conceivable, however, such as a switch which operates by sensing ultraviolet rays, heat, or the like. Therefore, the index of the second embodiment is applicable as an element that indicates a position of one of the above switches to specify a position to irradiate the ultraviolet rays or the heat.

Modification of Second Embodiment

Figure 9:
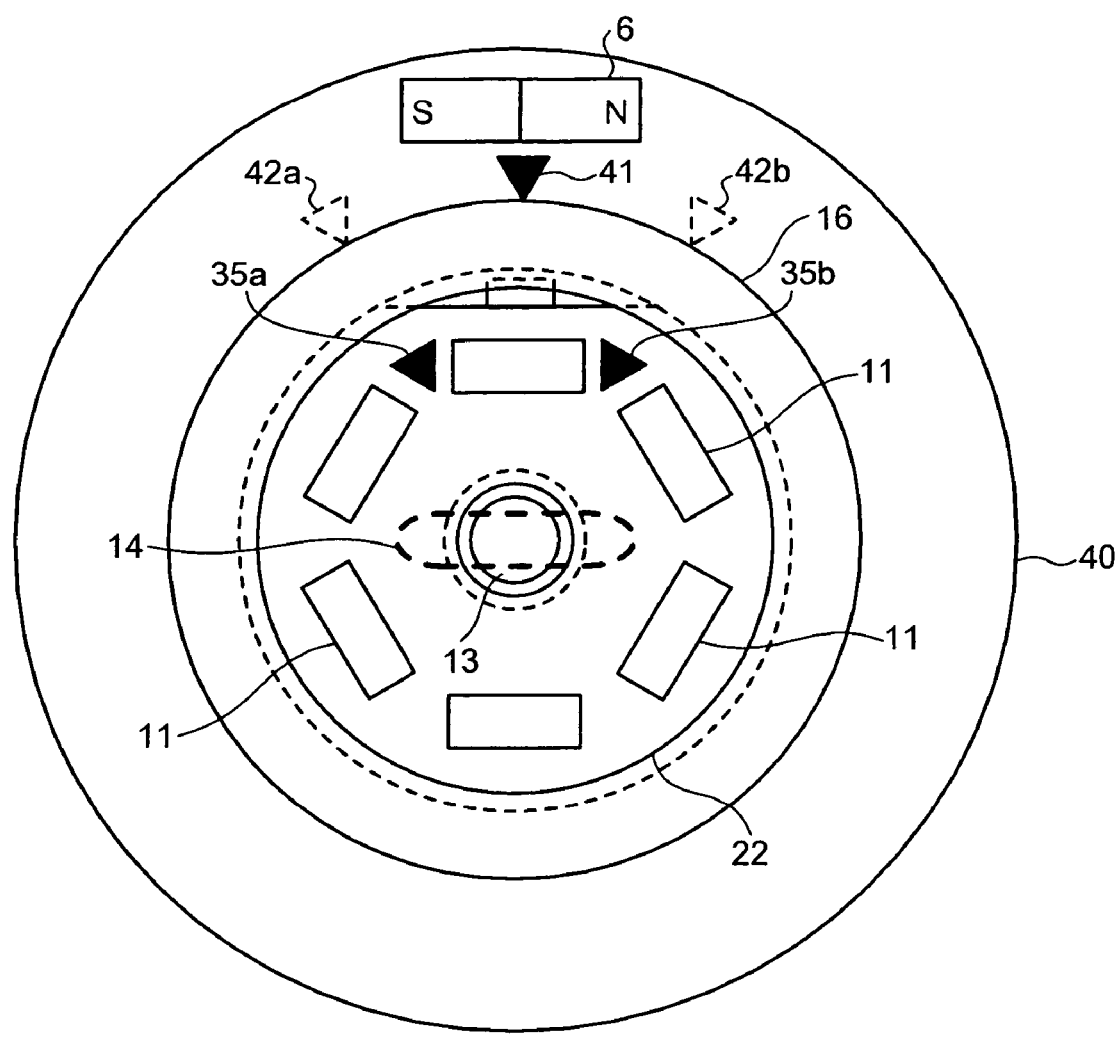
FIG. 9 shows a capsule endoscope set in a starter according to a modification of the second embodiment, in which the capsule endoscope is viewed from a similar angle to the angle of FIG. 8.

FIG. 9 shows the capsule endoscope 103 set in a starter 40 according to a modification of the second embodiment, and is a section viewed from the same direction as that of FIG. 8. In the modification of the second embodiment shown in FIG. 9, the indexes 35*a* and 35*b* arranged on the front face of the illuminating board 22 are the same as those of the second embodiment. The modification is different from the second embodiment in that the magnet 6 is arranged on the starter 40 and that an index 41 is arranged on the starter 40 in such a manner that the index 41 consisting of a triangular pattern indicating a position where the magnet 6 is arranged is aligned with the center of the magnet 6. In other respects, the structure of the modification is the same as that of the second embodiment, and the same component will be denoted by the same reference character.

In the modification of the second embodiment, the capsule endoscope 103 is set in the starter 40, and the magnet 6 is brought close to the predetermined position determined based on the indexes 35*a* and 35*b* of the capsule endoscope 103 (for example, the index 41 of the starter 40 is positioned right at the middle of two indexes 35*a* and 35*b* of the capsule endoscope 103 as shown in FIG. 9), so that the capsule endoscope 103 is driven, whereby the extending direction of the leads of the reed switch 14 becomes substantially parallel to the direction of the magnetic field of the magnet 6, and the leads 14*d* and 14*e* of the reed switch 14 and the movable electrodes 14*b* and 14*c* are magnetized to be different poles according to the magnetic induction of the magnetic field of the magnet 6. The magnetization causes one end of the movable electrode 14*b* and one end of the movable electrode 14*c* to move and contact with each other.

As can be seen from the foregoing, in the modification of the second embodiment, the indexes 35*a* and 35*b* are arranged within the range recognizable from the outside of the capsule endoscope 103 so as to indicate the direction of the magnetic field to be applied to the reed switch 14, and further, the index 41 is arranged on the starter 40 in which the capsule endoscope 103 is set so as to indicate the position where the magnet 6 is to be arranged. When the magnet 6 is brought close to the predetermined position determined based on the indexes 35*a*, 35*b*, and 41, the magnetic field of the magnet 6 in the starter 40 is applied in a direction parallel to the extending direction of the leads of the reed switch 14 similarly to the second embodiment, whereby the movable electrodes 14*b* and 14*c* are moved and made to contact with each other according to the magnetic induction of the magnetic field. As a result, the power supply from the power supply unit 15 to the function executing unit 10 is allowed. Therefore, the operator can easily check the orientation of the reed switch from outside to realize the on/off operations of the reed switch, whereby the operation of the capsule endoscope (more specifically, the operation of the function executing unit 10) can be initiated securely and easily.

In the modification of the second embodiment, the single index 41 is provided in the starter 40. The present invention, however, is not limited thereto. For example, indexes 42*a* and 42*b* shown by a dotted line in FIG. 9 may be provided on an extension from the center of the disk-like illuminating board 22 passing through the indexes 35*a* and 35*b* in a predetermined radial direction. At the time of the power supply to the function executing unit 10, the starter 40 or the capsule endoscope 103 may be shifted so that the indexes 42*a* and 42*b* are positioned at the predetermined radial direction (i.e., so that the indexes 35*a* and 35*b* on the side of the capsule endoscope 103 and the indexes 42*a* and 42*b* on the side of the starter 40 are arranged in the predetermined positional relation, so that the magnetic induction of the magnetic field of the magnet 6 works on the movable electrodes of the reed switch 14.

A current-carrying control method of the capsule endoscope according to the modification of the second embodiment is similar to the current-carrying control method of the second embodiment except that the direction of the magnetic field (direction of the magnet 6) relative to the reed switch 14 is recognized through visual confirmation of the index (e.g., indexes 35*a* and 35*b*) of the capsule endoscope side and the index (e.g., index 41 or indexes 42*a* and 42*b*) of the starter side at the direction recognizing step.

Third Embodiment

Figure 10:
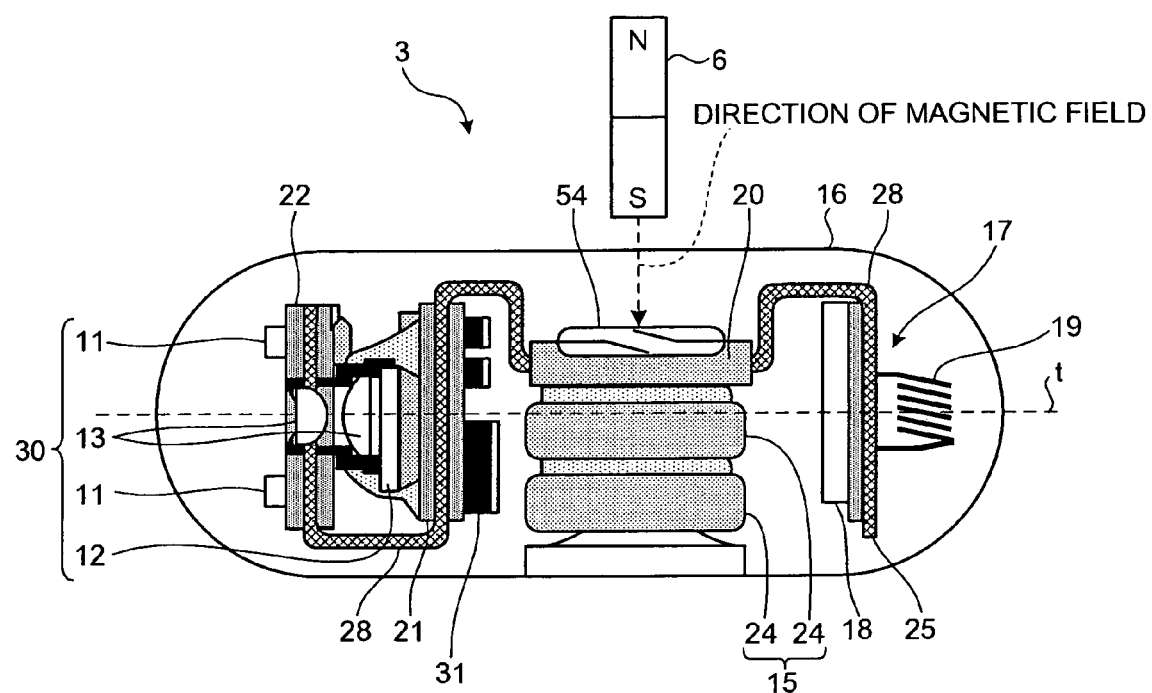
FIG. 10 is a sectional view showing an internal structure of a capsule endoscope according to a third embodiment of the present invention.
Figure 11:
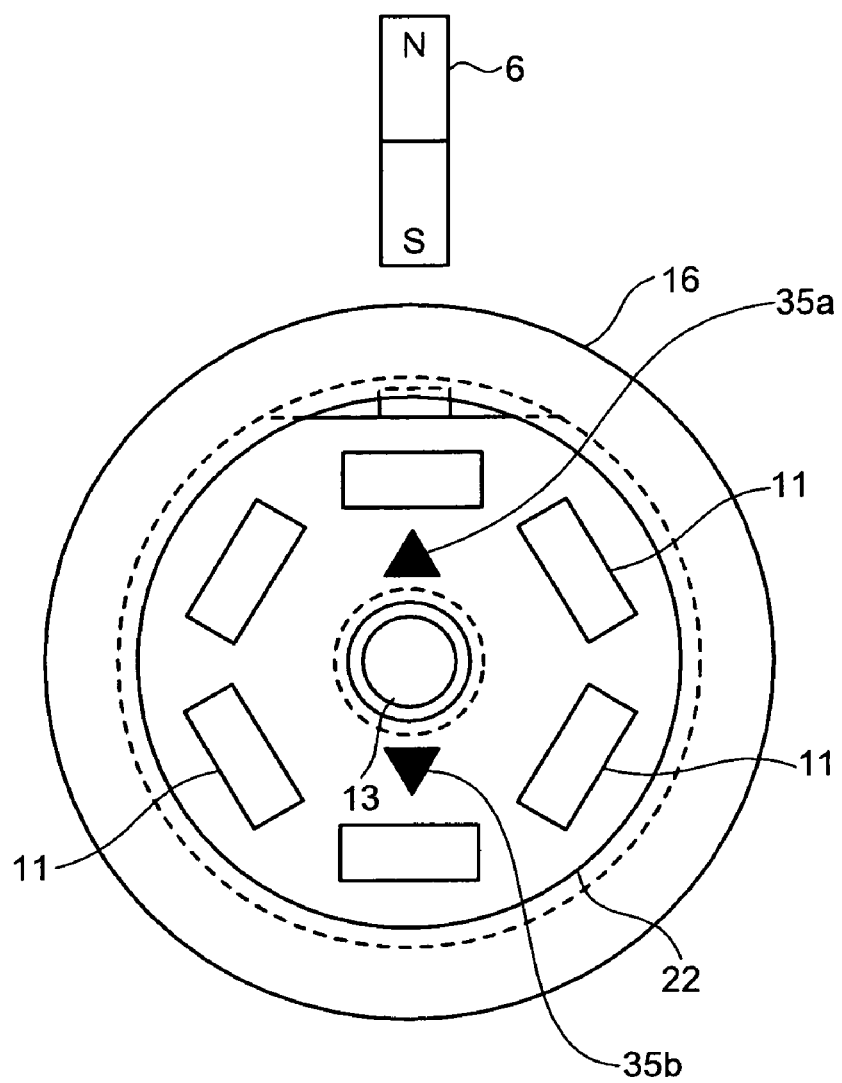
FIG. 11 shows the capsule endoscope of FIG. 10 viewed from a distal-end side where an image sensor is provided.

FIG. 10 is a sectional view of an internal structure of the capsule endoscope 203 according to a third embodiment of the present invention. FIG. 11 is a sectional view of the capsule endoscope 203 shown in FIG. 10 viewed from the distal-end side where the image sensor 30 is provided. As shown in FIG. 10, the capsule endoscope 203 according to the third embodiment includes a reed switch 54 which performs on/off operations according to the magnetic induction of a magnetic field which is substantially vertical to the extending direction of leads, in place of the reed switch 14 (which makes the movable electrodes 14*b* and 14*c* contact with each other or separate from each other according to the magnetic induction of the magnetic field parallel to the extending direction of leads) described above. Further, as shown in FIG. 11, two triangular indexes 35*a* and 35*b* are arranged within a range recognizable from the outside together with six LEDs 11 on the front surface of the disk-like illuminating board 22. The indexes 35*a* and 35*b* indicate in a manner recognizable from outside the direction of the magnetic field of the magnet 6 necessary to make the pair of contacts of the reed switch 54 contact with each other or separate from each other. In the third embodiment, the indexes 35a and 35b show the direction vertical to the direction of the longitudinal axis t of the capsule-like casing 16 (i.e., radial direction of the capsule-like casing 16) as the direction of the magnetic field of the magnet 6 approaching the reed switch 54 from outside the capsule-like casing 16. In other words, when the magnetic field is to be applied to the reed switch 54, the magnet 6 is brought close to the capsule endoscope 203 while the direction of the magnetic field is kept vertical to the direction of the longitudinal axis t (see FIGS. 10 and 11). In other respects, the structure of the third embodiment is the same as the structure of the first embodiment, and the same element will be denoted by the same reference character.

Figure 12:
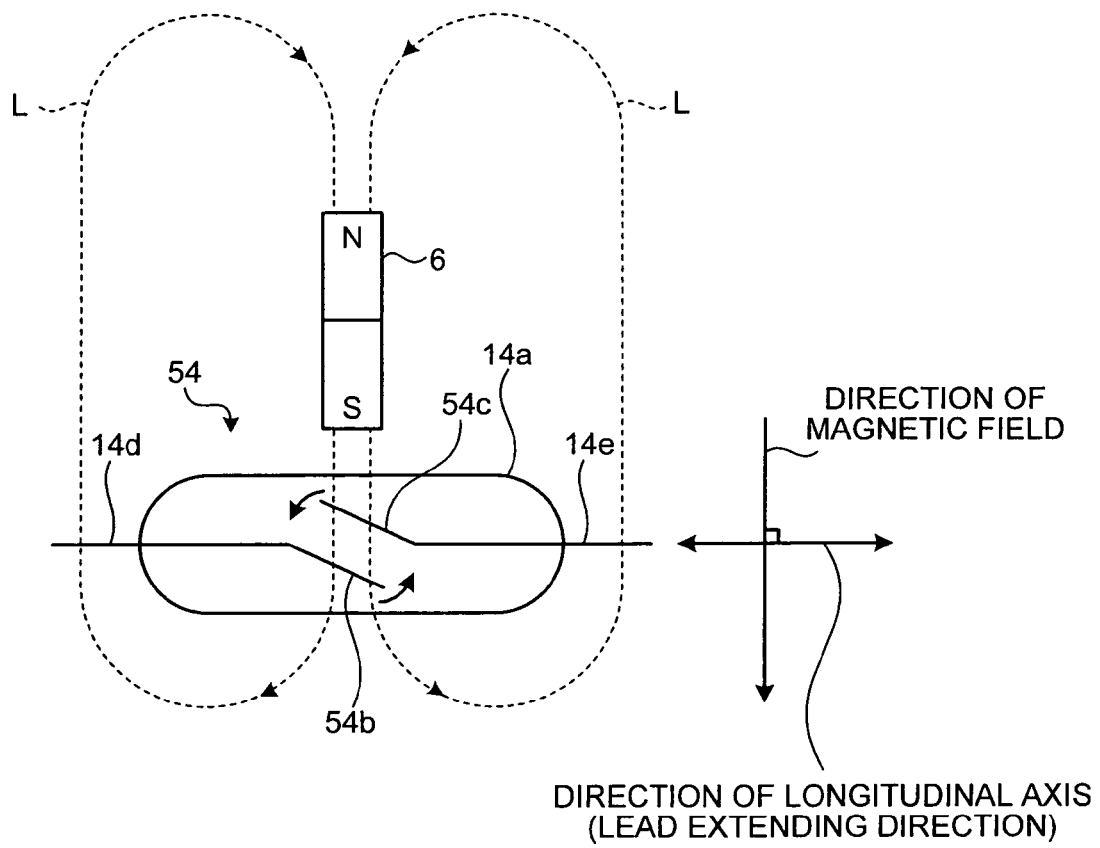
FIG. 12 is a schematic enlarged view of a structure of a reed switch which operates according to magnetic induction of a magnetic field vertical to the lead extending direction.
Figure 13:
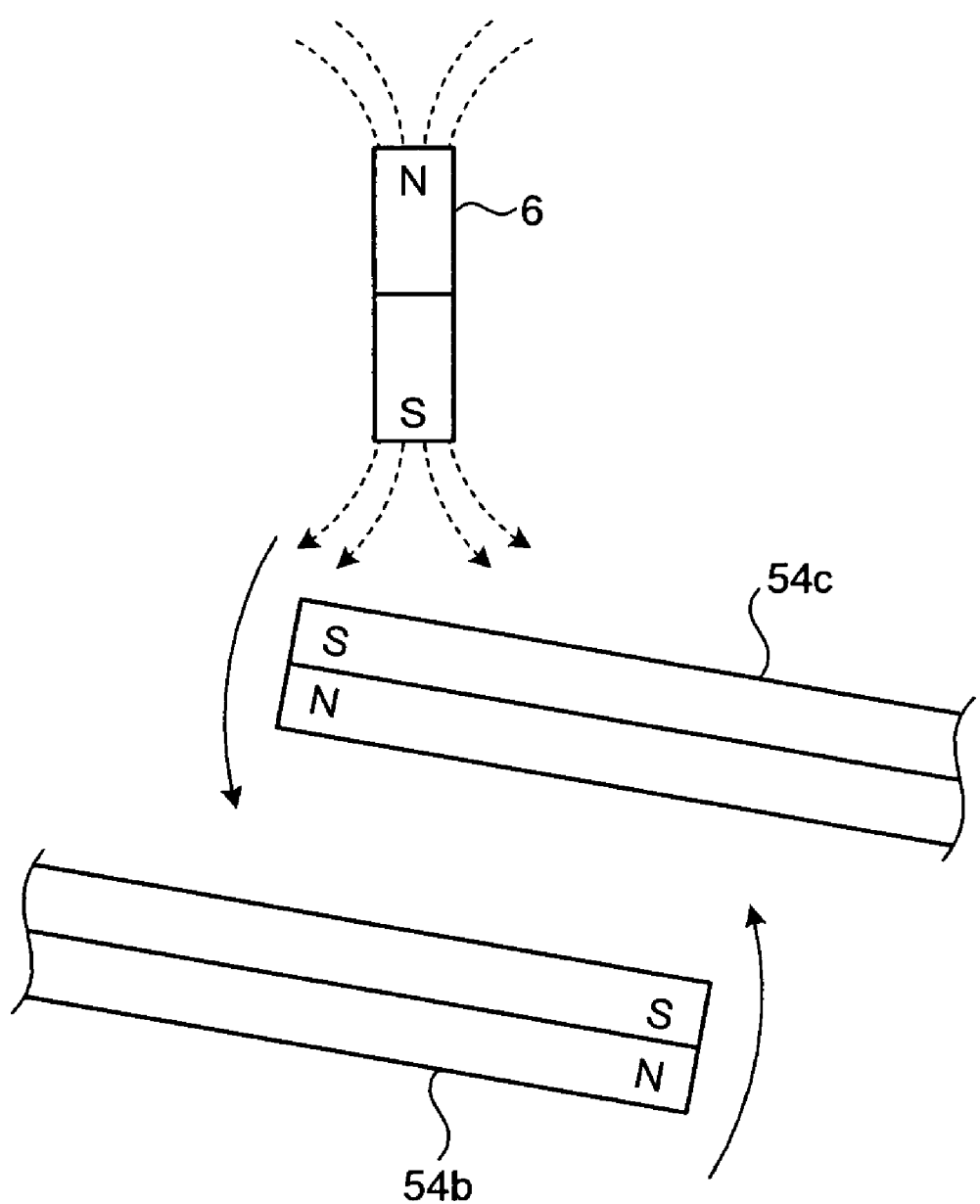
FIG. 13 is a schematic enlarged view of the reed switch of FIG. 12 in which movable electrodes are magnetized.

The reed switch 54 of the capsule endoscope 203 according to the third embodiment of the present invention will be described. FIG. 12 is a schematic enlarged view of the structure of the reed switch 54 which operates according to the magnetic induction of the magnetic field vertical to the extending direction of the leads. FIG. 13 is a schematic enlarged view of the reed switch 54 shown in FIG. 12 in a state where the movable electrodes are magnetized.

As shown in FIG. 12, the reed switch 54 includes an external casing 14a which consists of a substantially cylindrical glass tube or the like, leads 14d and 14e that extend from the external casing 14a, and movable electrodes 54b and 54c arranged inside the external casing 14a and connected to the leads 14d and 14e, respectively. The movable electrodes 54b and 54c are ends of the leads 14d and 14e, respectively, and work as a pair of contacts that is brought into contact according to the magnetic induction of the magnetic field substantially vertical to the direction of the longitudinal axis t of the capsule-like casing 16. The movable electrodes 54b and 54c are, similarly to the leads 14d and 14e, formed of an electrically conductive, magnetic material, and inserted from the outside into the external casing 14a along the central axis thereof for the arrangement.

The movable electrodes 54b and 54c are magnetized to be different poles along a direction of layers (thickness direction of the electrode) according to the magnetic induction of the magnetic field L generated by the approaching magnet 6. Specifically, as shown in FIG. 13, the movable electrodes 54b and 54c are magnetized so that the N-pole and the S-pole are alternately layered along the thickness direction of the electrode according to the magnetic field of the magnet 6 applied in the direction vertical to the direction of the longitudinal axis t of the capsule-like casing 16. A face of the movable electrode 54b and a face of the movable electrode 54c facing with each other are magnetized to be different poles. For example, as shown in FIG. 13, an opposing face on the movable electrode 54b side is magnetized to the S-pole, whereas an opposing face on the movable electrode 54c side is magnetized to the N-pole. When the movable electrodes 54b and 54c are magnetized to be different poles along the direction of layers, the movable electrodes 54b and 54c move as if being pulled towards each other and contact as shown by solid arrows in FIGS. 12 and 13.

The reed switch 54 having the above structure is arranged on the surface of the switching board 20 so that the extending direction of leads is substantially parallel to the direction of the longitudinal axis t of the capsule-like casing 16, similarly to the reed switch 14 of the first embodiment described earlier. Here, the leads 14d and 14e of the reed switch 54 are soldered to wires (not shown), for example, on the switching board 20, and are electrically connected to the function executing unit 10 and the power supply unit 15 via the wires. When the movable electrodes 14b and 14c of the reed switch 54 contact magnetically with each other as described above, the power from the power supply unit 15 is supplied to the function executing unit 10 via the reed switch 54 so as to enable the operation of each element for function execution. Alternatively, the reed switch 54 can be arranged on the surface of the flexible board 28 rather than on the switching board 20 so that the extending direction of the leads is substantially parallel to the direction of the longitudinal axis t of the capsule-like casing 16.

In the third embodiment, the indexes 35a and 35b indicate in a manner recognizable from outside the direction of the magnetic field of the magnet 6 necessary to make the movable electrodes 54b and 54c, i.e., the pair of contacts of the reed switch 54, operate (contact with each other or separate from each other). Specifically, the indexes 35a and 35b show, in a visually recognizable manner, the direction of the magnet 6 (direction of the N-pole and the S-pole) at the time the magnet 6 is brought close to the capsule-like casing 16 to make the movable electrodes 54b and 54c of the reed switch 54 contact with each other or separate from each other for the switching of the on/off state of the power supply from the power supply unit 15 to the function executing unit 10. The operator can easily recognize the direction of the magnet 6 approaching the capsule-like casing 16 (direction of the magnetic field to be applied to the reed switch 54) by visually checking the indexes 35a and 35b.

As exemplified by the indexes 35a and 35b, a direction index indicating the direction of the magnetic field applied to the reed switch 54 can be arranged at any position as far as the index can be visually recognized from outside of the capsule endoscope 203. For example, the index may be formed on an outer wall of the capsule-like casing 16 and not on the illuminating board 22 mentioned above.

When the magnet 6 is brought close to a predetermined position substantially at the center of the capsule endoscope 203 based on the indexes 35a and 35b (for example, when an S-pole end of the magnet 6 is brought close to a substantial center of the capsule endoscope 203 while the direction from the N-pole to the S-pole of the magnet 6 is kept substantially aligned with the direction from the index 35a to the index 35b as shown in FIGS. 10 and 11), the movable electrodes 54b and 54c of the reed switch 54 are magnetized to be different poles along the layer direction according to the magnetic induction of the magnetic field of the magnet 6, and as a result of the magnetization, the movable electrodes 54b and 54c move so that the opposing faces thereof come into contact with each other.

A current-carrying control method of the capsule endoscope according to the third embodiment will be described. As shown in FIG. 10 mentioned above, the capsule endoscope 203 is formed so that the function executing unit 10 (image sensor 30, radio unit 17, signal processing/control unit 31, and the like) and the reed switch 54 are arranged inside the capsule-like casing 16. The reed switch 54 has the movable electrodes 54b and 54c that are movable in response to an application of a magnetic field vertical to the extending direction of the leads. The reed switch 54 is arranged within the capsule-like casing 16 of the substantially cylindrical capsule endoscope 203 which is formed in a rotationally symmetrical shape about the direction of the longitudinal axis t, so that the extending direction of the leads is substantially parallel to the direction of the longitudinal axis t (switch unit arranging step). Here, the direction of the magnetic field which works on the reed switch 54 (i.e., the direction of the magnetic field of the magnet 6 which is brought close to the reed switch 54 from outside the capsule endoscope 203) is vertical to the direction of the longitudinal axis t of the capsule-like casing 16. The reed switch 54 is electrically connected to the function executing unit 10 and the power supply unit 15 as described above.

Then the operator recognizes the direction of the magnetic field of the magnet 6 which works on the reed switch 54 by visually checking the indexes 35a and 35b formed on the capsule endoscope 203 (e.g., illuminating board 22) (direction recognizing step). The indexes 35a and 35b are, as shown in FIG. 11, formed on the illuminating board 22 inside the capsule endoscope 203, and show in a visually recognizable manner the direction of the magnetic field of the magnet 6 (i.e., the direction of the N-pole to the S-pole of the magnet 6) which works on the reed switch 54 to make the movable electrodes 54b and 54c of the reed switch 54 contact with each other or separate from each other to control the conduction state or the conduction-shielded state of the function executing unit 10 and the power supply unit 15.

Thereafter, the magnet 6 outside the capsule endoscope 203 is brought close to or away from the reed switch 54 to magnetically operate the reed switch 54, whereby the conduction state or the conduction-shielded state between the function executing unit 10 and the power supply unit 15 via the reed switch 54 is controlled (current-carrying control step). In the current-carrying control step, as shown in FIG. 11, the direction from the N-pole to the S-pole of the magnet 6 is aligned with the direction from the index 35a to the index 35b, when the magnet 6 is brought close to a predetermined position substantially at the center of the capsule endoscope 203. When the magnet 6 enters the operable range of the reed switch 54, the magnetic field which is substantially vertical to the extending direction of leads (i.e., substantially vertical to the direction t of the longitudinal axis t) of the reed switch 54 is applied to the reed switch 54 from the magnet 6, and the surfaces of the movable electrodes 54b and 54c of the reed switch 54 opposite to each other are magnetized to be different poles (N-pole, S-pole), respectively, according to the magnetic induction of the magnetic field of the magnet 6. Due to the magnetization, the movable electrodes 54b and 54c are pulled toward each other, and as a result, the power supply unit 15 and the function executing unit 10 are turned from the conduction shielded state to the electrically connected state (conduction state) via the reed switch 54. In the conduction state, the power supply from the power supply unit 15 to the function executing unit 10 is allowed.

Thus, in the third embodiment, the indexes 35a and 35b are provided so as to indicate the direction of the magnetic field of the magnet 6 necessary to move (to bring close to or to separate) the movable electrodes 54b and 54c which is a pair of contacts of the reed switch 54 within a range recognizable from outside the capsule endoscope 203. When the magnet 6 is brought close to the reed switch 54 so that the direction defined by the indexes 35a and 35b is substantially equal to the direction of the magnetic field, the direction of the magnetic field of the external magnet 6 becomes vertical to the extending direction of leads of the reed switch 54. Then, the magnetic field is applied in the above direction to the reed switch 54, whereby the movable electrodes 54b and 54c can be made to move and contact with each other according to the magnetic induction of the magnetic field. As a result, the power supply from the power supply unit 15 to the function executing unit 10 is allowed, and the orientation of the reed switch can be easily confirmed from the outside so as to cause the on/off operations of the reed switch to securely and readily start the operation of the capsule endoscope (specifically, to start the operation of the function executing unit 10).

In the third embodiment, the direction of the magnetic field of the magnet 6 is indicated by the indexes 35a and 35b. The present invention, however, is not limited thereto, and the direction of the magnetic field of the magnet 6 may be indicated via a change in position or orientation of other element, similarly to the second embodiment described above.

Further, though the reed switch which is operable according to the magnetic field is described in the third embodiment, other switch which operates by sensing ultraviolet rays or heat, for example, may be employed, and the index of the second embodiment can be applied to an element which indicates the position of such a switch to specify a position which is to be irradiated with the ultraviolet rays or the heat.

The capsule medical apparatus and the current-carrying control method of the present invention define the direction of the magnetic field in a visually recognizable manner based on the direction of the longitudinal axis of the capsule-like casing or the direction index, and the switch connects the function executing unit and the power supply unit to allow conduction or to shield the conduction according to the magnetic field of the direction defined; thus, the capsule medical apparatus and the current-carrying control method of the present invention are advantageous in that the operation of the function executing unit of the capsule medical apparatus can be readily started.

In the first to the third embodiment and the modifications described above, electric current is made to flow from the power supply unit 15 to the function executing unit 10 for the power supply. The present invention, however, is not limited thereto, and the present invention can be applied to a structure in which the similar operation serves to shield the conduction from the power supply unit 15 to the function executing unit 10, thereby stopping the power supply.

Further, in the first to the third embodiments and the modifications described above, the capsule endoscope (an example of the capsule medical apparatus serving as the body-insertable apparatus) which acquires images in a living body is described. The present invention, however, is not limited thereto, and the present invention can be applied to a capsule medical apparatus which acquires information such as pH and temperature of the living body in the living body, exerting the similar effect and advantage as those obtained in the first to the third embodiments and the modifications described above.

Further, in the first to the third embodiments and the modifications described above, the magnet 6 that applies the magnetic field to the switch (e.g., reed switches 14 and 54) that connects the power supply unit and the function executing unit to allow conduction or to shield the conduction can be a permanent magnet or an electromagnet.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

INDUSTRIAL APPLICABILITY

As can be seen from the foregoing, the capsule medical apparatus and the current-carrying control method according to the present invention are useful for a capsule medical apparatus which is provided with a switch that switches the connection state between the function executing unit and the power supply unit according to the magnetic field, and in particular, are suitable for a capsule medical apparatus and a current-carrying control method which allows for easy visual confirmation of the direction of the magnetic field applied to the switch based on the direction of the longitudinal axis of the capsule-like casing or the direction index so as to allow for a readily initiation of the operation of the function executing unit.

What is claimed is:

1. A capsule medical apparatus comprising:
   a function executing unit that executes a predetermined function;
   a power supply unit that supplies power to the function executing unit;
   a main capsule body that houses the function executing unit and the power supply unit;
   a switch that is housed in the main capsule body, that has a pair of contacts which come into contact with each other and separate from each other according to a magnetic induction of a magnetic field applied from an outside of the main capsule body, and that connects the function executing unit and the power supply unit via the pair of contacts to allow conduction or to shield conduction; and
   a direction index that is visible from outside the capsule medical apparatus, and that indicates a direction of the magnetic field which causes contact and separation of the pair of contacts; wherein the function executing unit has an illuminating unit which emits illuminating light, the main capsule body further houses an illumination board provided with the illuminating unit, and the direction index is formed on the illumination board in such a manner that the direction of the magnetic field can be visually recognized from the outside of the main capsule body.

2. The capsule medical apparatus according to claim 1, wherein
   the switch is a reed switch, and
   the reed switch is arranged so that a lead extending direction is vertical to a direction of a longitudinal axis of the main capsule body.

3. The capsule medical apparatus according to claim 1, wherein
   the main capsule body is substantially cylindrical in shape and is formed in a rotationally symmetrical shape about a direction of a longitudinal axis, and
   the switch is arranged parallel to the direction of the longitudinal axis.

4. The capsule medical apparatus according to claim 1, wherein
   the direction index is formed inside the main capsule body or on an outer wall portion of the main capsule body in such a manner that the direction of the magnetic field can be visually recognized from the outside of the main capsule body.

* * * * *